United States Patent [19]

Kelly

[11] Patent Number: 5,326,498

[45] Date of Patent: Jul. 5, 1994

[54] AROMATIC ESTERS AND LIQUID CRYSTAL MIXTURES CONTAINING SAME

[75] Inventor: Stephen Kelly, Möhlin, Switzerland

[73] Assignee: Hoffmann-La Roche Inc., Nutley, N.J.

[21] Appl. No.: 969,619

[22] Filed: Oct. 30, 1992

[30] Foreign Application Priority Data

Nov. 8, 1991 [CH] Switzerland ............. 3273/91
Jun. 18, 1992 [CH] Switzerland ............. 1927/92

[51] Int. Cl.$^5$ ............. C09K 19/34; C07D 239/02; C07D 213/62
[52] U.S. Cl. ............. 252/299.61; 252/299.01; 252/299.67; 544/298; 546/290; 546/301
[58] Field of Search ............. 252/299.01, 299.61, 252/299.66, 299.67; 544/242, 298; 546/290, 301

[56] References Cited

U.S. PATENT DOCUMENTS

| | | | |
|---|---|---|---|
| 4,892,676 | 1/1990 | Sakurai et al. | 252/299.61 |
| 5,167,859 | 12/1992 | Wächtler et al. | 252/299.61 |

FOREIGN PATENT DOCUMENTS

| | | |
|---|---|---|
| 260077 | 3/1988 | European Pat. Off. . |
| 289270 | 11/1988 | European Pat. Off. . |
| 306195 | 3/1989 | European Pat. Off. . |
| 313338 | 4/1989 | European Pat. Off. . |
| 319167 | 6/1989 | European Pat. Off. . |
| 347941 | 12/1989 | European Pat. Off. . |
| 356672 | 3/1990 | European Pat. Off. . |
| 401522 | 12/1990 | European Pat. Off. . |
| 427166 | 5/1991 | European Pat. Off. . |
| 257638 | 6/1988 | Fed. Rep. of Germany . |
| 3939982 | 12/1989 | Fed. Rep. of Germany . |

OTHER PUBLICATIONS

Shibata et al., Chem. Abstracts 110:125661n (1989).
Krone et al., Liquid Crystals, vol. 2 (No. 4) pp. 411–422 (1987).
Derwent Abstract 88-244356/35 (1988) for DD 257 638.
Fukumasa et al., "Fluoro compounds, manufacture of their intermediates, and liquid crystal compositions containing the fluoro compounds", Chem. Abs. 116:162680n (1992).

(List continued on next page.)

Primary Examiner—Shean Wu
Attorney, Agent, or Firm—George M. Gould; George W. Johnston; Robert A. Silverman

[57] ABSTRACT

Compounds of the general formula

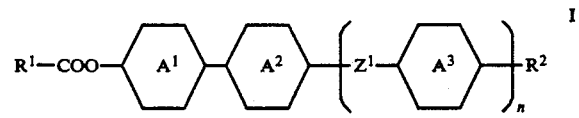

wherein
  $R^1$ signifies alkyl or alkenyl with 1 to 12 and, respectively, 2 to 12 carbon atoms, which is unsubstituted or mono- or multiply-substituted with halogen and in which one methylene group can be replaced by —O—;
  $R^2$ signifies alkyl or alkenyl with 1 to 12 and, respectively, 2 to 12 carbon atoms, which is unsubstituted or mono- or multiply-substituted with halogen and in which one or more methylene groups can be replaced by —O— and/or —COO— or —OOC—;
  $Z^1$ signifies a single covalent bond or —CH$_2$CH$_2$—;
  $A^1$, $A^2$ each independently represent 1,4-phenylene, which is unsubstituted or mono- or multiply-substituted with halogen, or pyridine-2,5-diyl or pyrimidine-2,5-diyl;
  $A^3$ represents 1,4-phenylene, which is unsubstituted or mono- or multiply-substituted with halogen, or pyridine-2,5-diyl, pyrimidine-2,5-diyl or trans-1,4-cyclohexylene;
  n is 0 or 1;

with the proviso that at least one of rings $A^1$, $A^2$ or $A^3$ signifies either pyridine-2,5-diyl or pyrimidine-2,5-diyl; and with the further proviso that, when n=0, $R^1$ represents 1E-alkenyl and $R^2$ represents alkyl, alkoxy or alkenyloxy, their manufacture and use in electro-optical devices as well as mixtures which contain said compounds are described in the present application.

7 Claims, No Drawings

OTHER PUBLICATIONS

Heppke et al., "The S$_M$ phase: evidence for a new type of tilted smectic phase", Mol. Cryst. Liq. Cryst. 208:9–19 (1991).

Shiratori et al., "New ferroelectric liquid crystals having 2-fluoro-2-methyl alkanoyloxy group", Mol. Cryst. Liq. Cryst. 199:129–140 (1991).

Bomelburg et al., "Synthesis and ferroelectric properties of 2,5-diphenyloyrimidines with different α-fluorocarboxylic acids", Zeitschrift fur Naturforschung B, 44:1127–1131 (1989).

Shibata et al., "Optically active citronellic acid esters and ferroelectric liquid-crystal compositions containing the esters", Chem. Abs. 113:201537f (1990).

Myazawa et al., "2,5-Diphenylpyrimidine derivatives, liquid crystal compositions containing them, and electrooptical display devices", Chem. Abs. 111:205651v (1989).

Murayama et al., "Liquid crystal materials containing phenylpyrimidine derivatives and display elements therefrom", Chem. Abs. 110:125654n (1989).

Matsumoto et al., "Multiplexed ferroelectric liquid crystal display", Ferroelectrics 85:235–254 (1988).

Fukumasa et al., "Optically active (phenylpyrimidinyl) phenyl propionate derivative and liquid crystal composition containing same", Chem. Abs. 115:244241p (1991).

Shionozaki et al., "Biphenylpyridine derivatives as ferroelectric liquid crystals", Chem. Abs. 110:223266g (1989).

Shiratori et al., "Biphenylpyrimidinyl esters and liquid-crystal compositions containing them", Chem. Abs. 117:161126v (1992).

Murayama et al., "Preparation of optically-active lactic acid aryl esters and liquid crystal devices using them", Chem. Abs. 116:162678t (1992).

Fukumasa et al., "Phenylpyrimidinylphenyl esters for liquid crystal compositions", Chem. Abs. 117:121719j (1992).

Kelly et al., "Liquid-Crystal Transition Temperatures and Physical Properties of Some New Alkenyl-substituted phenylpyrimidine and phenylpyridine Esters", J. Mater. Chem., 3(9), 953–963 1993.

AROMATIC ESTERS AND LIQUID CRYSTAL MIXTURES CONTAINING SAME

FIELD OF THE INVENTION

The present invention is concerned with aromatic esters, liquid crystalline mixtures which contain such compounds as well as their use for electro-optical purposes.

BACKGROUND

Liquid crystals are used primarily as dielectrics in indicating devices, since the optical properties of such substances can be influenced by an applied voltage. Electro-optical devices based on liquid crystals are well-known to a person skilled in the art and can be based on various effects. Examples of such devices are cells having dynamic scattering, DAP cells (deformation of aligned phases), SSF cells (surface stabilized ferroelectric), DHF cells (deformed helix ferroelectric) or SBF cells (short-pitch bistable ferroelectric).

The liquid crystal materials must have a good chemical and thermal stability and a good stability towards electric fields and electromagnetic radiation. Further, the liquid crystal materials should have low viscosity and in the cells should give short response times and a high contrast. Furthermore, at usual operating temperatures of about $-30°$ C. to about $+80°$ C., especially of about $-20°$ C., to about $+60°$ C., they should have a suitable mesophase, for example a broad smectic mesophase for the cells referred to above.

Since liquid crystals are usually used as mixtures of several components, it is important that the components have a good miscibility with one another.

SUMMARY OF THE INVENTION

The present invention now provides compounds which are extremely suitable for such liquid crystal mixtures. These compounds have the general formula

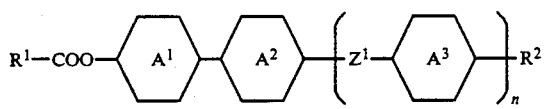

I wherein
- $R^1$ signifies alkyl or alkenyl with 1 to 12 and, respectively, 2 to 12 carbon atoms, which is unsubstituted or mono- or multiply-substituted with halogen and in which one methylene group can be replaced by —O—;
- $R^2$ signifies alkyl or alkenyl with 1 to 12 and, respectively, 2 to 12 carbon atoms, which is unsubstituted or mono- or multiply-substituted with halogen and in which one or more methylene groups can be replaced by —O— and/or —COO— or —OOC—;
- $Z^1$ signifies a single covalent bond or —CH$_2$CH$_2$—;
- $A^1$, $A^2$ each independently represent 1,4-phenylene, which is unsubstituted or mono- or multiply-substituted with halogen, or pyridine-2,5-diyl or pyrimidine-2,5-diyl;
- $A^3$ represents 1,4-phenylene, which is unsubstituted or mono- or multiply-substituted with halogen, or pyridine-2,5-diyl, pyrimidine-2,5-diyl or trans-1,4-cyclohexylene;
- n is 0 or 1;

with the proviso that at least one of rings $A^1$, $A^2$ or $A^3$ signifies either pyridine-2,5-diyl or pyrimidine-2,5-diyl; and with the further proviso that, when n=0, $R^1$ represents 1E-alkenyl and $R^2$ represents alkyl, alkoxy or alkenyloxy.

It has surprisingly been found that the compounds in accordance with the invention have extremely favourable mesophases for ferroelectric applications.

Upon admixing the compounds of general formula I in accordance with the invention there is frequently brought about in liquid crystal mixtures a considerable increase of the $S_C$-$S_A$, $S_C$-N, $S_A$-I or N-I phase transition and the melting point is significantly lowered, which leads to a broad smectic mesophase. The compounds in accordance with the invention have broad smectic mesophases with amazingly low viscosity. Thus, the switching times of basic mixtures can be lowered considerably by the addition of such compounds. The compounds in accordance with the invention which contain two rings have been found to be outstanding components for $S_C$ mixtures in spite of their nematic phase. They narrow the $S_A$ phase and induce a nematic phase without lowering the $S_C$ phase transition. In this manner there are obtained phases which can be aligned optimally and which are thus excellently suited for SSF applications.

The term "alkyl or alkenyl with 1 to 12 and, respectively, 2 to 12 carbon atoms, which is unsubstituted or mono- or multiply-substituted with halogen and in which one methylene group can be replaced by —O—" signifies in the scope of the present invention groups such as alkyl, alkoxy, alkenyl, alkenyloxy, alkoxyalkyl, alkenyloxyalkyl, alkoxyalkenyl with 1 to 12 and, respectively, 2 to 12 carbon atoms. These groups can be unbranched or branched; they are preferably unbranched. These groups can be mono- or multiply-substituted with halogen, especially with fluorine. Such groups are, for example, methyl, ethyl, propyl, butyl, pentyl, hexyl, isopropyl, 2-methyl-butyl, 2-methyl-pentyl, 3-methyl-butyl, 3-methyl-pentyl, 4-methyl-pentyl, methoxy, ethoxy, propyloxy, butyloxy, pentyloxy, hexyloxy, methoxypropyl, methoxybutyl, methoxypentyl, ethoxypropyl, ethoxybutyl, propyloxypropyl, 1E-propenyl, 1E-butenyl, 1E-pentenyl, 1E-hexenyl, 1E-heptenyl, 1E-octenyl, 1E-nonenyl, 1E-decenyl, 1E-undecenyl and the like.

The term "alkyl or alkenyl with 1 to 12 and, respectively, 2 to 12 carbon atoms, which is unsubstituted or mono- or multiply-substituted with halogen and in which one or more methylene groups can be replaced by —O— and/or —COO— or —OOC—" signifies in the scope of the present invention inter alia groups as previously defined. In addition, this term embraces alkenyl groups such as 2Z-butenyl, 2Z-pentenyl, 2Z-hexenyl, 3-butenyl, 3E-pentenyl, 3E-hexenyl, 4-pentenyl, 4Z-hexenyl, 5-hexenyl, allyloxy, 2E-butenyloxy, 3-butenyloxy, 2E-pentenyloxy, 3Z-pentenloxy, 4-pentenyloxy, 2E-hexenyloxy, 3Z-hexenyloxy, 4E-hexenyloxy, 2E-heptenyloxy, 2E-octenyloxy, 2E-nonenyloxy, 2E-decenyloxy, 2E-undecenyloxy, 2E-dodecenyloxy, allyloxypropyl, 3-butenyloxypropyl and also branched or preferably unbranched groups which contain in the chain in place of an oxygen atom, or also additionally thereto, a carboxyl group. Such groups are, for example, alkoxycarbonyl, alkanoyloxy, alkoxycarbonylalkyl or alkanoyloxyalkyl, alkenyloxy, alkenyloxycarbonyl and the like. These groups can be mono- or multiply-substituted with halogen, especially with fluorine. Such groups are, for example, acetoxy, propanoyloxy, butanoyloxy, pentanoyloxy, hexanoyloxy, ethoxycarbonyl, propyloxycarbonyl, butyloxycarbonyl, pentyloxycarbonyl, hexyloxycarbonyl, 2E-butenoyloxy 2E-pentenoyloxy, 2E-hexenoyloxy, 2E-heptenoyloxy, 2E-octenoyloxy, 2E-nonenoyloxy, 2E-decenoyloxy, 2E-undecenoyloxy, 2E-dodecenoyloxy, allyloxycarbonyl, 2-butenyloxycarbonyl, 3-butenyloxycarbonyl, 2-pentenyloxycarbonyl, 3-pentenyloxycarbonyl, 4-pentenyloxycarbonyl and the like. Here, however, groups with 1 to 7 and, respectively, 2 to 7 carbon atoms are preferred.

The term "1,4-phenylene, which is unsubstituted or mono- or multiply-substituted with halogen," embraces in the scope of the present invention 1,4-phenylene, 2-fluoro-1,4-phenylene, 3-fluoro-1,4-phenylene, 2,3-difluoro-1,4-phenylene and the like, but especially 1,4-phenylene or 2,3-difluoro-1,4-phenylene.

The term "halogen" embraces in the scope of the present invention fluorine, chlorine, bromine and iodine, but especially fluorine.

DESCRIPTION OF THE PREFERRED EMBODIMENTS

Preferred compounds of general formula I are compounds of the formulae

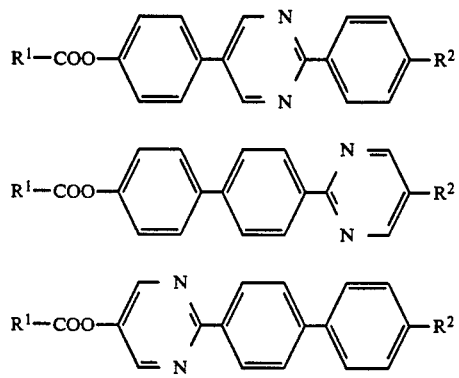

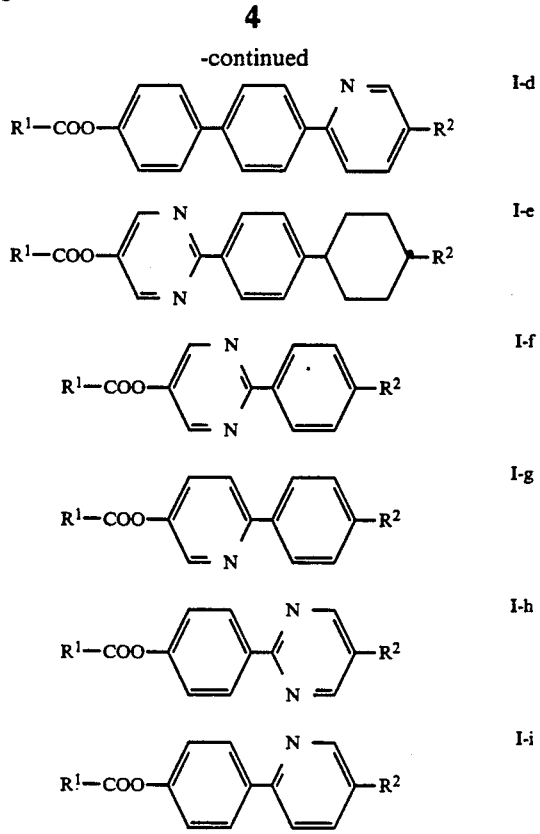

wherein $R^1$ and $R^2$ have the above significance.

The compounds of general formula I in accordance with the invention are readily accessible synthetically and can be manufactured in a manner known per se from phenols or 5-hydroxypyridines or 5-hydroxypyrimidines and an acid. The esterification can be effected, for example, in the presence of N,N'-dicyclohexylcarbodiimide and 4-(dimethylamino)pyridine in dichloromethane or another suitable solvent such as e.g. chloroform. The starting materials are known and are in part commercially available or they can be prepared as indicated in Schemes 1 to 3 hereinafter.

Scheme 1

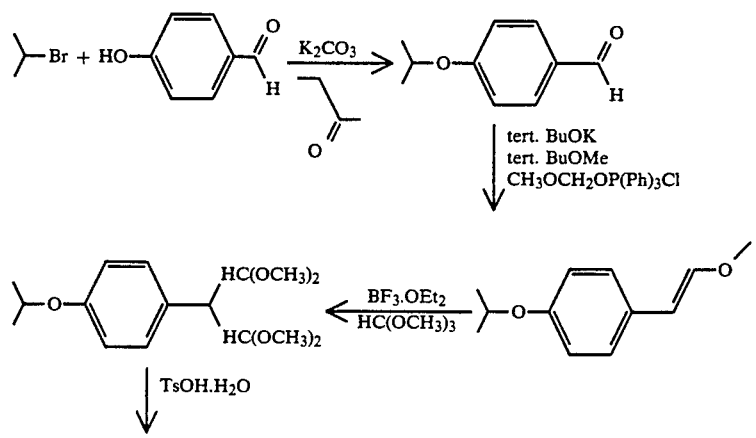

5,326,498
-continued
Scheme 1
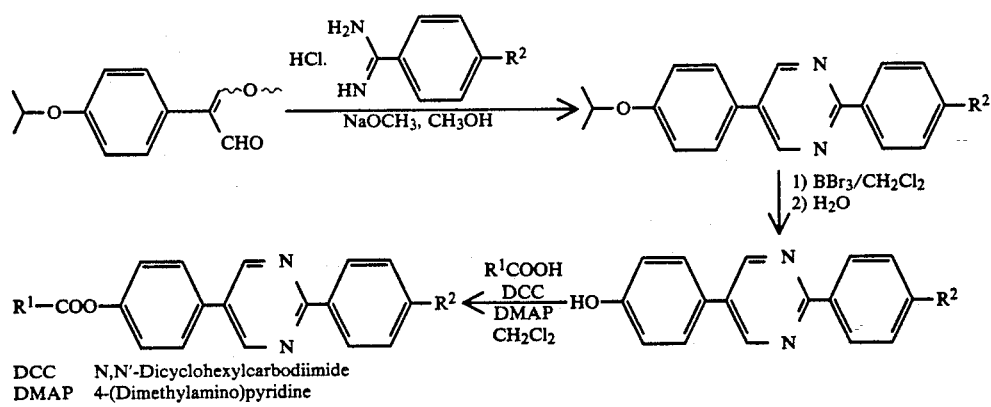
DCC  N,N'-Dicyclohexylcarbodiimide
DMAP  4-(Dimethylamino)pyridine
Scheme 2
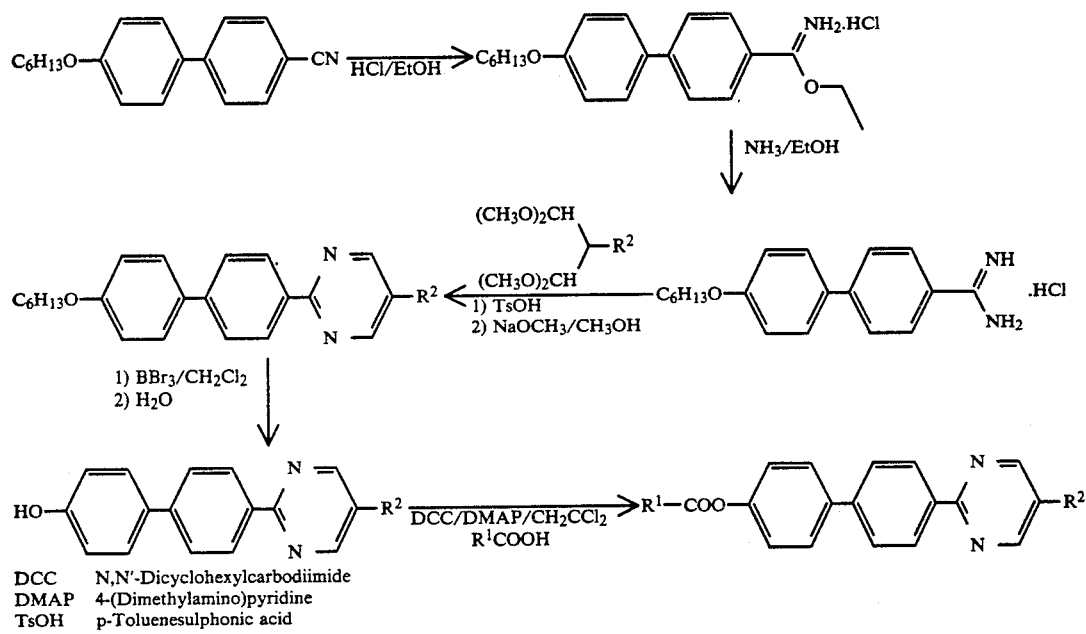
DCC  N,N'-Dicyclohexylcarbodiimide
DMAP  4-(Dimethylamino)pyridine
TsOH  p-Toluenesulphonic acid
Scheme 3
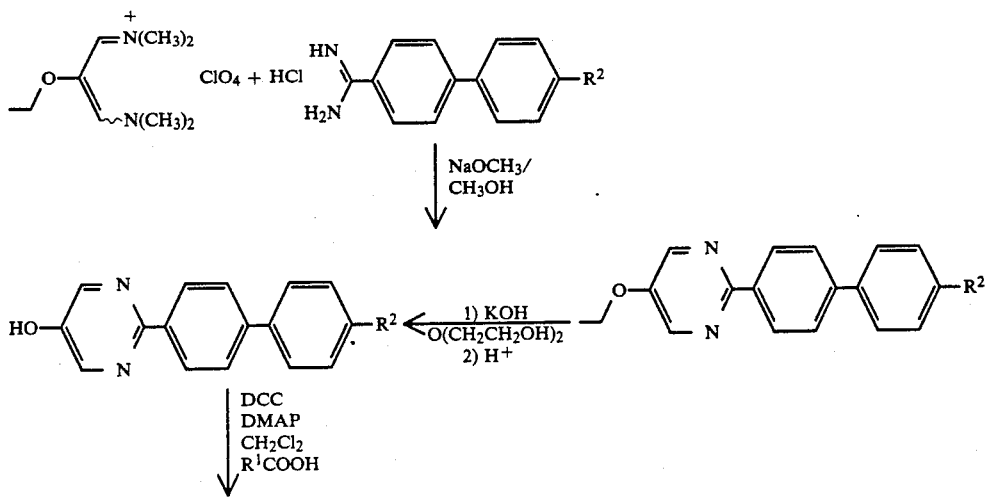

Scheme 3

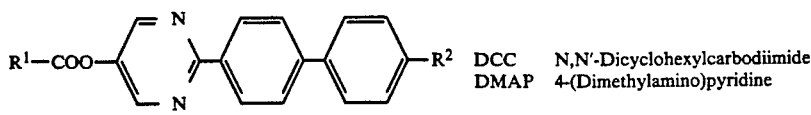

DCC    N,N'-Dicyclohexylcarbodiimide
DMAP    4-(Dimethylamino)pyridine

The compounds of formula I can be used in the form of mixtures with one another and/or with other liquid crystal components.

The liquid crystalline mixtures in accordance with the invention contain at least 2 components of which at least one component is a compound of formula I. A second component and optionally additional components can be further compounds of formula I or other known liquid crystalline compounds. However, in each case at least one chiral component must be present in the mixture. When one of the components used is not already chiral, a chiral dopant must therefore be added.

Such liquid crystal components are preferably achiral compounds of the formulae

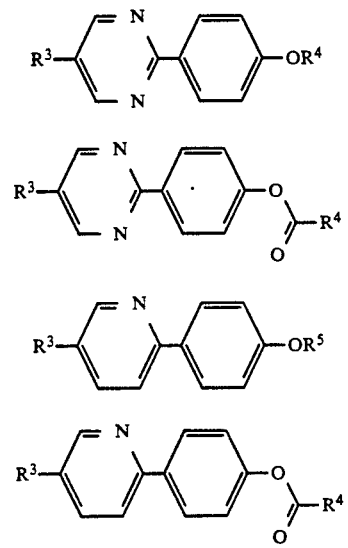

II

III

IV

V and, respectively, chiral dopants of the general formulae

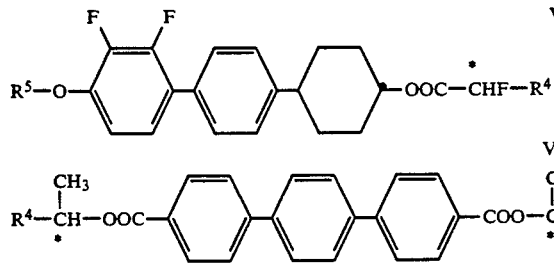

VI

VII wherein $R^3$ represents alkyl or alkoxyl; $R^4$ signifies alkyl; and $R^5$ signifies alkyl or alkenyl.

The term "alkyl" in connection with the compounds of formulae II to VII embraces unbranched or branched alkyl groups with 1 to 12 carbon atoms, preferably unbranched alkyl groups with 6 to 12 carbon atoms such as hexyl, heptyl, octyl, nonyl, decyl, undecyl, dodecyl.

The term "alkoxy" embraces ether groups in which the alkyl residue is as defined previously.

The term "alkenyl" embraces in connection with the compounds of fomulae II–VII alkenyl groups with 2 to 15 carbon atoms such as 2E-alkenyl, 3Z-alkenyl, 4E-alkenyl and alkenyl having a terminal double bond. The terms "2E-alkenyl", "3Z-alkenyl" and "4E-alkenyl" preferably embrace unbranched alkenyl groups with 3 to 9, 4 to 9 and, respectively, 5 to 9 carbon atoms in which the double bond is present in the 2, 3 and, respectively, 4 position, whereby E and Z denote the configuration of the double bond. Such groups are, for example, 2E-butenyl, 2E-pentenyl, 2E-hexenyl, 2E-heptenyl, 2E-octenyl, 2E-nonenyl, 3-butenyl, 3Z-pentenyl, 3Z-hexenyl, 3Z-heptenyl, 3Z-octenyl, 3Z-nonenyl, 4-pentenyl, 4E-hexenyl, 4E-heptenyl, 4E-octenyl, 4E-nonenyl, 5-hexenyl, 6-heptenyl, 7-octenyl, 8-nonenyl and the like.

Having regard to the good solubility of the compounds of formula I and having regard to their good miscibility with one another, the content of compounds of formula I in the mixtures in accordance with the invention can be relatively high and can be up to about 85 wt. %. In general, a content of about 1–50, especially 5–30, wt. % of compounds of formula I is preferred.

The manufacture of the liquid crystalline mixtures and of the electro-optical devices can be effected in a manner known per se.

The invention is illustrated in more detail by the following Examples. In the Examples C signifies a crystalline phase, N signifies a nematic phase, Ch signifies a chiral nematic phase, S signifies a smectic phase and I signifies the isotropic phase.

EXAMPLE 1

0.8 g of N,N'-dicyclohexylcarbodiimide is added within 5 minutes while stirring to a solution of 1.0 g of 4-(2-[4-pentylphenyl]-5-pyrimidinyl)phenol, 0.4 g of caproic acid and 0.05 g of 4-(dimethylamino)pyridine in 30 ml of dichloro-methane. The reaction mixture is stirred overnight, then filtered, the filtrate is washed with saturated sodium bicarbonate solution and with water and concentrated. Chromatography of the residue on silica gel with hexane/ethyl acetate (vol. 4:1) and two-fold recrystallization of the fractions which are pure according to thin-layer chromatography give 1.0 g of 4-(2-[4-pentylphenyl]-5-pyrimidinyl)phenyl hexanoate; m.p. (C-$S_C$) 124° C., phase transition ($S_C$-$S_A$) 185° C., cl.p. ($S_A$-I) 224° C.

The 4-(2-[4-pentylphenyl]-5-pyrimidinyl)phenol used as the starting material is prepared as follows:

a) A solution of 30 g of 4-hydroxybenzaldehyde and 46 g of isopropyl bromide in 300 ml of N,N-dimethylformamide is treated with 104 g of finely powdered potassium carbonate and the mixture is stirred at 58° C. overnight. The suspension is suction filtered and the filtrate is concentrated in a vacuum. A solution of the residue in 100 ml of diethyl ether is washed twice with 100 ml of water each time, dried over sodium sulphate and concentrated. Chromatography of the crude product on silica gel with hexane/ethyl acetate (vol. 9:1) gives 40 g of 4-(isopropyloxy)benzaldehyde.

b) A suspension of 140 g of methoxymethyl-triphenylphosphonium chloride in 400 ml of tert.-butyl methyl ether is treated with 45 g of potassium tert.-butylate within 5 minutes at 0° C. while gassing with nitrogen and the mixture is stirred for a further 10 minutes. Then, a solution of 41 g of 4-(isopropyloxy)-benzaldehyde in 100 ml of tert.-butyl methyl ether is added dropwise at 0° C. within 30 minutes. The reaction mixture is stirred at room temperature for a further 16 hours and then poured into 750 ml of 0.8N sodium hydrogen carbonate solution. The aqueous phase is separated and back-extracted with diethyl ether. The organic phase is washed neutral with water, dried over magnesium sulphate and concentrated. The residue is suspended in 800 ml of hexane. After cooling to 0° C. the triphenylphosphine oxide is filtered off and the filtrate is concentrated. Chromatography of the residue on silica gel with hexane/ethyl acetate (vol. 9:1) gives 45 g of pure 1-methoxy-2-(4-[isopropoxy]phenyl)ethene.

c) Firstly 10 ml of boron trifluoride diethyl etherate and subsequently 48 g of 1-methoxy-2-(4-[isopropoxy]phenyl)ethene are added dropwise under a nitrogen atmosphere at 0° C. to 273 ml of trimethyl orthoformate. The reaction mixture is stirred at 0°0 C. for a further 4 hours and then neutralized with 6 ml of triethanolamine and concentrated. The residue is taken up in 500 ml of diethyl ether and the solution is washed with 100 ml of saturated sodium bicarbonate solution and twice with 150 ml of water each time, dried over magnesium sulphate, filtered and concentrated. Chromatography of the residue on silica gel with hexane/ethyl acetate (vol. 9:1) and distillation at 135°-137° C. (1 mm Hg) give 44 g of (4-[isopropoxyphenyl)malonaldehyde tetramethyl acetal.

d) A mixture of 20.9 g of (4-[isopropoxy]phenyl)-malonaldehyde tetramethyl acetal, 5.0 g of p-toluenesulphonic acid monohydrate and 1.5 ml of water is heated to 70°-80° C. for 2 hours under a nitrogen atmosphere, then treated with 0.3 g of sodium bicarbonate, stirred for a further 5 minutes and filtered. The filter residue is rinsed with methanol and the filtrate containing crude 2-(methoxymethylidene)-2-(4-[isopropoxyphenyl)acetaldehyde is used immediately in the next step.

e) A sodium methylate solution freshly prepared from 14.7 ml of methanol and 2.5 g of sodium is added dropwise under a nitrogen atmosphere to a mixture of 15.0 g of p-pentylbenzamidine hydrochloride, 75 ml of methanol and the above methanolic solution of 2-(methoxymethylidene)-2-(4-[isopropoxy]phenyl)acetaldehyde. The reaction mixture is stirred overnight and subsequently adjusted to pH 3–4 with concentrated hydrochloric acid. The separated 5-(4-isopropyloxyphenyl)-2-(4-pentylphenyl)pyrimidine is filtered off, washed with water and with methanol and dried in a vacuum. Chromatography of the residue on silica gel with dichloromethane/hexane (vol. 91:1) gives 6.6 g of pure product.

f) A solution of 5.5 g of boron tribromide in 50 ml of absolute dichloromethane is treated dropwise at 0° C. with a solution of 6.5 g of 5-(4-isopropyloxyphenyl)-2-(4-pentylphenyl)pyrimidine in 50 ml of absolute dichloromethane. The mixture is stirred for 24 hours and then poured on to ice-water. The organic phase is separated and the aqueous phase is back-extracted three times with 50 ml of dichloromethane each time. The combined organic phases are washed with 50 ml of 2N sodium carbonate solution and several times with water, dried over magnesium sulphate and concentrated. Chromatography of the residue on silica gel with dichloromethane/methanol (vol. 99:1 ) and recrystallization from hexane give 5.2 g of 4-(2-[4-pentylphenyl]-5-pyrimidinyl)phenol with m.p. 152°–153° C.

The following compounds can be manufactured in an analogous manner:

4-(2-[4-Propylphenyl]-5-pyrimidinyl)phenyl acetate;
4-(2-[4-propylphenyl]-5-pyrimidinyl)phenyl propionate;
4-(2-[4-propylphenyl]-5-pyrimidinyl)phenyl butanoate;
4-(2-[4-propylphenyl]-5-pyrimidinyl)phenyl pentanoate;
4-(2-[4-propylphenyl]-5-pyrimidinyl)phenyl hexanoate;
4-(2-[4-propylphenyl]-5-pyrimidinyl)phenyl heptanoate;
4-(2-[4-pentylphenyl]-5-pyrimidinyl)phenyl acetate, m.p. (C-$S_C$) 169° C., $S_C$-$S_A$ 137° C., $S_A$-N 179° C., cl.p. (N-I) 222° C.;
4-(2-[4-pentylphenyl]-5-pyrimidinyl)phenyl propionate, m.p. (C-$S_C$) 150° C., $S_C$-$S_A$ 166° C., $S_A$-N 217° C., cl.p. (N-I) 230° C.;
4-(2-[4-pentylphenyl]-5-pyrimidinyl)phenyl butanoate, m.p. (C-$S_C$) 143° C., $S_C$-$S_A$ 170° C., $S_A$-N 225° C., cl.p. (N-I) 229° C.;
4-(2-[4-pentylphenyl]-5-pyrimidinyl)phenyl pentanoate, m.p. (C-$S_C$) 139° C., $S_C$-$S_A$ 184° C., cl.p. ($S_A$-I) 224° C.;
4-(2-[4-pentylphenyl]-5-pyrimidinyl)phenyl hexanoate, m.p. (C-$S_3$) 124° C., $S_3$-$S_C$ 132° C., $S_C$-$S_A$ 184° C., cl.p. ($S_A$-I) 224° C.;
4-(2-[4-pentylphenyl]-5-pyrimidinyl)phenyl heptanoate;
4-(2-[4-pentylphenyl]-5-pyrimidinyl)phenyl octanoate, m.p. (C-$S_3$) 110° C., $S_3$-$S_C$ 134° C., $S_C$-$S_A$ 197° C., cl.p. ($S_A$-I) 217° C.;
4-(2-[4-heptylphenyl]-5-pyrimidinyl)phenyl acetate;
4-(2-[4-heptylphenyl]-5-pyrimidinyl)phenyl propionate;
4-(2-[4-heptylphenyl]-5-pyrimidinyl)phenyl butanoate;
4-(2-[4-heptylphenyl]-5-pyrimidinyl)phenyl pentanoate;
4-(2-[4-heptylphenyl]-5-pyrimidinyl)phenyl hexanoate;
4-(2-[4-heptylphenyl]-5-pyrimidinyl)phenyl heptanoate.

EXAMPLE 2

2.0 g of caproic acid, 5.0 g of 4-(4-[5-decyl-2-pyrimidinyl]phenyl)phenol, 3.0 g of N,N'-dicyclohexylcarbodiimide, 0.4 g of 4-(dimethylamino)pyridine and 100 ml of dichloromethane are reacted in an analogous manner to Example 1 to give 5 g of 4-(4-[5-decyl-2-pyrimidinyl]-4'-biphenyl) hexanoate with m.p. (C-$S_4$) 34° C., phase transition ($S_4$-$S_3$) 53° C., phase transition ($S_3$-$S_2$) 66° C., phase transition ($S_2$-$S_C$) 124° C., phase transition ($S_C$-N) 169° C. and cl.p. (N-I) 180° C.

The 4-(4-[5-decyl-2-pyrimidinyl]phenyl)phenol used as the starting material is prepared as follows:

a) A solution of 30 g of 4-cyano-4'-(pentyloxy)biphenyl, 23 ml of ethyl alcohol and 200 ml of toluene is placed at 0° C. and hydrogen chloride is introduced for 6 hours. The reaction mixture is stirred at room temperature for a further 48 hours, then concentrated and dried under a vacuum. This gives 39 g of ethyl 4-[4-(pentyloxy)phenyl]-benzimidate hydrochloride.

b) A mixture of 39 g of ethyl 4-[4-(pentyloxy)phenyl]-benzimidate hydrochloride and 100 ml of ethyl alcohol is placed at room temperature and gassed with nitrogen, then treated with 82.5 ml of saturated ethanolic ammonia solution and stirred overnight. The reaction mixture is concentrated, dried under a vacuum, suspended in diethyl ether, stirred at room temperature 2 hours, cooled to 0° C. and suction filtered. The white crystals are washed with diethyl ether and then dried under a vacuum. This gives 35.7 g of 4-(4-[pentyloxylphenyl)-benzamidine hydrochloride.

c) 44.5 g of 2-(decyl)malonaldehyde tetramethyl acetal, 17 g of p-toluenesulphonic acid monohydrate and 2 ml of water are reacted in an analogous manner to Example 1(d) to give 2-(methoxymethylidene)dodecanal.

d) 2-(Methoxymethylidene)dodecanal in 10 ml of methanol, 20.6 ml of 30% sodium methylate solution and 35.7 g of 4-(4-[pentyloxy]phenyl)benzamidine hydrochloride are reacted in an analogous manner to Example 1(e) to give 21.3 g of 5-decyl-2-(4-[pentyloxy]-4'-biphenyl)pyrimidine.

e) 21.3 g of 5-decyl-2-(4-[pentyloxy]-4'-biphenyl)-pyrimidine, 17.7 g of boron tribromide and 100 ml of dichloromethane are reacted in an analogous manner to Example 1(f) to give 12.5 g of 4-(4-[5-decyl-2pyrimidinyl]phenyl)phenol.

The following compounds can be manufactured in an analogous manner:

4-[5-Propyl-2-pyrimidinyl]-4'-biphenyl acetate;
4-[5-propyl-2-pyrimidinyl]-4'-biphenyl propanoate;
4-[5-propyl-2-pyrimidinyl]-4'-biphenyl butanoate;
4-[5-propyl-2-pyrimidinyl]-4'-biphenyl pentanoate;
4-[5-propyl-2-pyrimidinyl]-4'-biphenyl hexanoate;
4-[5-propyl-2-pyrimidinyl]-4'-biphenyl heptanoate;
4-[5-pentyl-2-pyrimidinyl]-4'-biphenyl acetate;
4-[5-pentyl-2-pyrimidinyl]-4'-biphenyl propanoate;
4-[5-pentyl-2-pyrimidinyl]-4'-biphenyl butanoate;
4-[5-pentyl-2-pyrimidinyl]-4'-biphenyl pentanoate;
4-[5-pentyl-2-pyrimidinyl]-4'-biphenyl hexanoate;
4-[5-pentyl-2-pyrimidinyl]-4'-biphenyl heptanoate;
4-[5-heptyl-2-pyrimidinyl]-4'-biphenyl acetate;
4-[5-heptyl-2-pyrimidinyl]-4'-biphenyl propanoate;
4-[5-heptyl-2-pyrimidinyl]-4'-biphenyl butanoate;
4-[5-heptyl-2-pyrimidinyl]-4'-biphenyl pentanoate;
4-[5-heptyl-2-pyrimidinyl]-4'-biphenyl hexanoate;
4-[5-heptyl-2-pyrimidinyl]-4'-biphenyl heptanoate;
4-[5-octyl-2-pyrimidinyl]-4'-biphenyl acetate;
4-[5-octyl-2-pyrimidinyl]-4'-biphenyl propanoate;
4-[5-octyl-2-pyrimidinyl]-4'-biphenyl butanoate;
4-[5-octyl-2-pyrimidinyl]-4'-biphenyl pentanoate;
4-[5-octyl-2-pyrimidinyl]-4'-biphenyl hexanoate;
4-[5-octyl-2-pyrimidinyl]-4'-biphenyl heptanoate;
4-[5-decyl-2-pyrimidinyl]-4'-biphenyl acetate;
4-[5-decyl-2-pyrimidinyl]-4'-biphenyl propanoate;
4-[5-decyl-2-pyrimidinyl]-4'-biphenyl butanoate;
4-[5-decyl-2-pyrimidinyl]-4'-biphenyl pentanoate;
4-[5-decyl-2-pyrimidinyl]-4'-biphenyl heptanoate;
1-(5-pentyl-2-pyrimidinyl)-4-phenyl (2E)-butenoate;
1-(5-pentyl-2-pyrimidinyl)-4-phenyl (2E)-pentenoate;
1-(5-pentyl-2-pyrimidinyl)-4-phenyl (2E)-hexenoate;
1-(5-pentyl-2-pyrimidinyl)-4-phenyl (2E)-heptenoate;
1-(5-pentyl-2-pyrimidinyl)-4-phenyl (2E)-octenoate;
1-(5-pentyl-2-pyrimidinyl)-4-phenyl (2E)-nonenoate;
1-(5-pentyl-2-pyrimidinyl)-4-phenyl (2E)-decenoate;
1-(5-pentyl-2-pyrimidinyl)-4-phenyl (2E)-undecenoate
1-(5-pentyl-2-pyrimidinyl)-4-phenyl (2E)-dodecenoate;
1-(5-hexyl-2-pyrimidinyl)-4-phenyl (2E)-butenoate;
1-(5-hexyl-2-pyrimidinyl)-4-phenyl (2E)-pentenoate;
1-(5-hexyl-2-pyrimidinyl)-4-phenyl (2E)-hexenoate;
1-(5-hexyl-2-pyrimidinyl)-4-phenyl (2E)-heptenoate;
1-(5-hexyl-2-pyrimidinyl)-4-phenyl (2E)-octenoate;
1-(5-hexyl-2-pyrimidinyl)-4-phenyl (2E)-nonenoate;
1-(5-hexyl-2-pyrimidinyl)-4-phenyl (2E)-decenoate;
1-(5-hexyl-2-pyrimidinyl)-4-phenyl (2E)-undecenoate;
1-(5-hexyl-2-pyrimidinyl)-4-phenyl (2E)-dodecenoate;
1-(5-heptyl-2-pyrimidinyl)-4-phenyl (2E)-butenoate, m.p. (C-I) 97° C., (N-I) (87° C.);
1-(5-heptyl-2-pyrimidinyl)-4-phenyl (2E)-pentenoate, m.p. (C-I) 104° C., (N-I) (69° C.);
1-(5-heptyl-2-pyrimidinyl)-4-phenyl (2E)-hexenoate, m.p. (C-N) 70° C., cl.p. (N-I) (82° C.);
1-(5-heptyl-2-pyrimidinyl)-4-phenyl (2E)-heptenoate, m.p. (C-N) 48° C., cl.p. (N-I) (72° C.);
1-(5-heptyl-2-pyrimidinyl)-4-phenyl (2E)-octenoate, m.p. (C-N) 50° C., cl.p. (N-I) 80° C.;
1-(5-heptyl-2-pyrimidinyl)-4-phenyl (2E)-nonenoate;
1-(5-heptyl-2-pyrimidinyl)-4-phenyl (2E)-decenoate, m.p. (C-N) 59° C., cl.p. (N-I) 80° C.;
1-(5-heptyl-2-pyrimidinyl)-4-phenyl (2E)-undecenoate;
1-(5-heptyl-2-pyrimidinyl)-4-phenyl (2E)-dodecenoate, m.p. (C-N) 52° C., cl.p. (N-I) 80° C.;
1-(5-octyl-2-pyrimidinyl)-4-phenyl (2E)-butenoate, m.p. (C-N) 65° C., cl.p. (N-I) 80° C.;
1-(5-octyl-2-pyrimidinyl)-4-phenyl (2E)-pentenoate, m.p. (C-I) 83° C., (N-I) (64° C.);
1-(5-octyl-2-pyrimidinyl)-4-phenyl (2E)-hexenoate, m.p. (C-N) 70° C., cl.p. (N-I) 76° C.;
1-(5-octyl-2-pyrimidinyl)-4-phenyl (2E)-heptenoate, m.p. (C-N) 54° C., cl.p. (N-I) 66° C.;
1-(5-octyl-2-pyrimidinyl)-4-phenyl (2E)-octenoate, m.p. (C-N) 46° C., cl.p. (N-I) 75° C.;
1-(5-octyl-2-pyrimidinyl)-4-phenyl (2E)-nonenoate;
1-(5-octyl-2-pyrimidinyl)-4-phenyl (2E)-decenoate, m.p. (C-N) 41° C., cl.p. (N-I) 76° C.;
1-(5-octyl-2 -pyrimidinyl) -4-phenyl (2E)-undecenoate;
1-(5-octyl-2-pyrimidinyl)-4-phenyl (2E)-dodecenoate, m.p. (C-N) 52° C., cl.p. (N-I) 78° C.
1-(5-nonyl-2-pyrimidinyl)-4-phenyl (2E)-butenoate, m.p. (C-N) 80° C., cl.p. (N-I) 89° C.;
1-(5-nonyl-2-pyrimidinyl)-4-phenyl (2E)-pentenoate, m.p. (C-I) 89° C., (N-I) (70° C.);
1-(5-nonyl-2-pyrimidinyl)-4-phenyl (2E)-hexenoate, m.p. (C-N) 68° C., cl.p. (N-I) 81° C.;
1-(5-nonyl-2-pyrimidinyl)-4-phenyl (2E)-heptenoate, m.p. (C-N) 47° C., cl.p. (N-I) 70° C.;
1-(5-nonyl-2-pyrimidinyl) -4-phenyl (2E)-octenoate, m.p. (C-N) 49° C., cl.p. (N-I) 79° C.;
1-(5-nonyl -2-pyrimidinyl)-4-phenyl (2E)-decenoate, m.p. (C-N) 50° C., cl.p. (N-I) 81° C.;
1-(5-nonyl -2-pyrimidinyl)-4-phenyl (2E)-undecenoate;
1-(5-nonyl -2-pyrimidinyl)-4-phenyl (2E)-dodecenoate, m.p. (C-N) 60° C., cl.p. (N-I) 82° C.

EXAMPLE 3

0.2 g of caproic acid, 0.4 g of 2-[4-pentyl-4'-biphenyl]-5-hydroxypyrimidine, 0.3 g of N,N'-dicyclohexylcarbodiimide, 0.04 g of 4-(dimethylamino)pyridine and 50 ml of dichloro- methane are reacted in an analogous manner to Example 1 to give 0.4 g of 2-[4-pentyl-4'biphenyl]-5-([hexanoyl]oxy)pyrimidine.

The 2-[4-pentyl-4'-biphenyl]-5-hydroxypyrimidine used as the starting material is prepared as follows:

a) A sodium methylate solution freshly prepared from 50 ml of methanol and 2.6 g of sodium is treated with 15 g of 4-(4-pentylphenyl)benzamidine hydrochloride and 13.5g of 1,3 -bis(dimethylamino)-2-ethoxytrimethinium perchlorate (Cell. Czech. Chem. Commun. 38, 1168, 1973) in 80 ml of methanol while gassing with nitrogen. The reaction mixture is heated under slight reflux for 5 hours, then poured into 100 ml of water, neutralized with concentrated hydrochloric acid and then extracted three times with 100 ml of diethyl ether each time. The combined organic phases are washed with 100 ml of concentrated sodium chloride solution, 100 ml of concentrated potassium carbonate solution and then again with 100 ml of concentrated sodium chloride solution, dried over magnesium sulphate, filtered and subsequently concentrated. The residue is chromatographed on silica gel with hexane/ethyl acetate (vol. 9:1) and then recrystallized from ethyl alcohol. This gives 14.7 g of pure 2-[4-pentyl -4'-biphenyl]-5-(ethoxy)pyrimidine.

b) A mixture of 14.7 g of 2-[4-pentyl-4-biphenyl]-5-(ethoxy)-pyrimidine, 17 g of sodium hydroxide and 120 ml of diethylene glycol is heated at 180 C. for 8 hours. The reaction mixture is poured into 100 ml of water, acidified with concentrated hydrochloric acid, then extracted three times with 50 ml of diethyl ether each time. The combined organic phases are washed twice with 100 ml of concentrated sodium chloride solution, dried over magnesium sulphate, filtered and subsequently concentrated. Chromatography of the residue on silica gel with hexane/ethyl acetate (vol. 7:3) and recrystallization from ethyl alcohol give 11 g of 2-[4-pentyl-4'-biphenyl]-5-hydroxypyrimidine.

The following compounds can be manufactured in an analogous manner:

2-[4-Propyl-4'-biphenyl]-5-(acetoxy)pyrimidine;
2-[4-propyl-4'-biphenyl]-5-([propanoyl]oxy)pyrimidine;
2-[4-propyl-4'-biphenyl]-5-([butanoyl]oxy)pyrimidine;
2-[4-propyl-4'-biphenyl]-5-([pentanoyl]oxy)pyrimidine;
2-[4-propyl-4'-biphenyl]-5-([hexanoyl]oxy)pyrimidine;
2-[4-propyl-4'-biphenyl]-5-([heptanoyl]oxy)pyrimidine;
2-[4-propyl-4'-biphenyl]-5-([octanoyl]oxy)pyrimidine;
2-[4-propyl-4'-biphenyl]-5-([nonanoyl]oxy)pyrimidine;
2-[4-propyl-4'-biphenyl]-5-([decanoyl]oxy)pyrimidine;
2-[4-propyl-4'-biphenyl]-5-([(E)-2-pentenoyl]oxy)-pyrimidine;
2-[4-propyl-4'-biphenyl]-5-([(Z)-3-pentenoyl]oxy)-pyrimidine;
2-[4-propyl-4'-biphenyl]-5-([4-pentenoyl]oxy)pyrimidine;
2-[4-pentyl-4'-biphenyl]-5-(acetoxy)pyrimidine;
2-[4-pentyl-4'-biphenyl]-5-([propanoyl]oxy)pyrimidine;
2-[4-pentyl-4'-biphenyl]-5-([butanoyl]oxy)pyrimidine;
2-[4-pentyl-4'-biphenyl]-5-([pentanoyl]oxy)pyrimidine;
2-[4-pentyl-4'-biphenyl]-5-([hexanoyl]oxy)pyrimidine;
2-[4-pentyl-4'-biphenyl]-5-([heptanoyl]oxy)pyrimidine;
2-[4-pentyl-4'-biphenyl]-5-([octanoyl]oxy)pyrimidine;
2-[4-pentyl-4'-biphenyl]-5-([nonanoyl]oxy)pyrimidine;
2-[4-pentyl-4'-biphenyl]-5-([decanoyl]oxy)pyrimidine;
2-[4-pentyl-4'-biphenyl]-5-([(E)-2-pentenoyl]oxy)-pyrimidine;
2-[4-pentyl-4'-biphenyl]-5-([(Z)-3-pentenoyl]oxy)-pyrimidine;
2-[4-pentyl-4'-biphenyl]- 5-([4-pentenoyl]oxy)pyrimidine;
2-[4-heptylphenyl]-5-[(2E-butenoyl)oxy]pyrimidine;
2-[4-heptylphenyl]-5-[(2E-pentenoyl)oxy]pyrimidine;
2-[4-heptylphenyl]-5-[(2E-hexenoyl)oxy]pyrimidine;
2-[4-heptylphenyl]-5-[(2E-heptenoyl)oxy]pyrimidine;
2-[4-heptylphenyl]-5-[(2E-octenoyl)oxy]pyrimidine, m.p. (C-N) 80° C., cl.p. (N-I) 86° C.;
2-[4-heptylphenyl]-5-[(2E-nonenoyl)oxy]pyrimidine;
2-[4-heptylphenyl]-5-[(2E-decenoyl)oxy]pyrimidine;
2-[4-heptylphenyl]-5-[(2E-undecenoyl)oxy]pyrimidine;
2-[4-heptylphenyl]-5-[(2E-dodecenoyl)oxy]pyrimidine;
2-[4-octylphenyl]-5-[(2E-butenoyl)oxy]pyrimidine;
2-[4-octylphenyl]-5-[(2E-pentenoyl)oxy]pyrimidine;
2-[4-octylphenyl]-5-[(2E-hexenoyl)oxy]pyrimidine;
2-[4-octylphenyl]-5-[(2E-heptenoyl )oxy]pyrimidine;
2-[4-octylphenyl]-5-[(2E-octenoyl)oxy]pyrimidine;
2-[4-octylphenyl]-5-[(2E-nonenoyl)oxy]pyrimidine;
2-[4-octylphenyl]-5-[(2E-decenoyl)oxy]pyrimidine;
2-[4-octylphenyl]-5-[(2E-undecenoyl)oxy]pyrimidine;
2-[4-octylphenyl]-5-[(2E-dodecenoyl)oxy]pyrimidine;
2-(4-[2-(4-pentylphenyl)ethyl]phenyl-5-(acetoxy)-pyrimidine;
2-(4-[2-(4-pentylphenyl)ethyl]phenyl-5-([propanoyl]oxy)pyrimidine;
2-(4-[2-(4-pentylphenyl)ethyl]phenyl-5-([butanoyl]oxy)-pyrimidine;
2-(4-[2-(4-pentylphenyl)ethyl]phenyl-5-([pentanoyl]oxy)pyrimidine;
2-(4-[2-(4-pentylphenyl)ethyl]phenyl-5-([hexanoyl]oxy)pyrimidine;
2-(4-[2-(4-pentylphenyl)ethyl]phenyl-5-([heptanoyl]oxy)-pyrimidine;
2-(4-[2-(4-pentylphenyl)ethyl]phenyl-5-([octanoyl]oxy)-pyrimidine;
2-[4-(trans-4-propylcyclohexyl)phenyl]-5-(acetoxy)-pyrimidine;
2-[4-(trans-4-propylcyclohexyl)phenyl]-5-([propanoyl]oxy)pyrimidine;
2-[4-(trans-4-propylcyclohexyl)phenyl]-5-([butanoyl]oxy)pyrimidine;
2-[4-(trans-4-propylcyclohexyl)phenyl]-5-([pentanoyl]oxy)pyrimidine;
2-[4-(trans-4-propylcyclohexyl)phenyl]-5-([hexanoyl]oxy)pyrimidine;
2-[4-(trans-4-propylcyclohexyl)phenyl]-5-([heptanoyl]oxy)pyrimidine;
2-[4-(trans-4-propylcyclohexyl)phenyl]-5-([octanoyl]oxy)pyrimidine;
2-[4-(trans-4-pentylcyclohexyl)phenyl]-5-(acetoxy)-pyrimidine;
2-[4-(trans-4-pentylcyclohexyl)phenyl]-5-([propanoyl]oxy)pyrimidine;
2-[4-(trans-4-pentylcyclohexyl)phenyl]-5-([butanoyl]oxy)pyrimidine;
2-[4-(trans-4-pentylcyclohexyl)phenyl]-5-([pentanoyl]oxy)pyrimidine;
2-[4-(trans-4-pentylcyclohexyl)phenyl]-5-([hexanoyl]oxy)pyrimidine;
2-[4-(trans-4-pentylcyclohexyl)phenyl]-5-([heptanoyl]oxy)pyrimidine, m.p. 112° C., cl.p. 188° C.;
2-[4-(trans-4-pentylcyclohexyl)phenyl]-5-([octanoyl]oxy)pyrimidine, m.p. (C-N) 120° C., cl.p. (N-I) 189° C.;
2-[4-(trans-4-pentylcyclohexyl)phenyl]-5-([nonanoyl]oxy)pyrimidine;
2-[4-(trans-4-pentylcyclohexyl)phenyl]-5-([decanoyl]oxy)pyrimidine;
2-[4-(trans-4-pentylcyclohexyl)phenyl]-5-([undecanoyl]oxy)pyrimidine, m.p. (C-N) 138° C., cl.p. (N-I) 169° C.;
2-[4-(trans-4-pentylcyclohexyl)phenyl]-5-([dodecanoyl]oxy)pyrimidine, m.p. (C-$S_C$) 120° C., $S_C$-N 138° C., cl.p. (N-I) 169° C.;
2-[4-(trans-4-heptylcyclohexyl)phenyl]-5-(acetoxy)-pyrimidine;
2-[4-(trans-4-heptylcyclohexyl)phenyl]-5-([propanoyl]oxy)pyrimidine;
2-[4-(trans-4-heptylcyclohexyl )phenyl]-5-([butanoyl]oxy)pyrimidine;
2-[4-(trans-4-heptylcyclohexyl)phenyl]-5-([pentanoyl]oxy)pyrimidine;

2-[4-(trans-4-heptylcyclohexyl)phenyl]-5-([hexanoyl]oxy)pyrimidine;
2-[4-(trans-4-heptylcyclohexyl)phenyl]-5-([heptanoyl]oxy)pyrimidine;
2-[4-(trans-4-heptylcyclohexyl)phenyl]-5-([octanoyl]oxy)pyrimidine;
2-(4-[2-(trans-4-pentylcyclohexyl)ethyl]phenyl-5-(acetoxy)pyrimidine;
2-(4-[2-(trans-4-pentylcyclohexyl)ethyl]phenyl-5-([propanoyl]oxy)pyrimidine
2-(4-[2-(trans-4-pentylcyclohexyl)ethyl]phenyl-5-([butanoyl]oxy)pyrimidine;
2-(4-[2-(trans-4-pentylcyclohexyl)ethyl]phenyl-5-([pentanoyl]oxy)pyrimidine;
2-(4-[2-(trans-4-pentylcyclohexyl)ethyl]phenyl-5-([hexanoyl]oxy)pyrimidine;
2-(4-[2-(trans-4-pentylcyclohexyl)ethyl]phenyl-5-([heptanoyl]oxy)pyrimidine;
2-(4-[2-(trans-4-pentylcyclohexyl)ethyl]phenyl-5-([octanoyl]oxy)pyrimidine.

EXAMPLE 4

0.25 g of caproic acid, 1.0 g of 4-(5-pentyl-2-pyridinyl)-4'-hydroxybiphenyl, 0.8 g of N,N'-dicyclohexylcarbodiimide, 0.04 g of 4-(dimethylamino)pyridine and 50 ml of dichloromethane are reacted in an analogous manner to Example 1 to give 4-(5-pentyl-2-pyridinyl)-4'-biphenyl hexanoate.

The 4-(5-pentyl-2-pyridinyl)-4'-biphenyl hexanoate used as the starting material is prepared as follows:

a) 20 g of 4-bromo-4'-hydroxybiphenyl, 12 g of isopropyl bromide, 45 g of potassium carbonate and 200 ml of N,N'-dimethylformamide are reacted in an analogous manner to Example 1(a) to give 18 g of 4-bromo-4'-(isopropoxy)biphenyl.

b) A Grignard reagent prepared from 0.8 g of magnesium, 10 g of 4-bromo-4'-(isopropoxy)biphenyl and 50 ml of tetrahydrofuran is added dropwise at 0°14 5° C. within 30 minutes to a mixture of 7.5 g of crude 2-chloro-5-[(tetrahydro-2-pyranyloxy)methyl]pyridine, 75 ml of tetrahydrofuran and 0.36 g of 1,3-bis(diphenylphosphino)propanenickel(II) chloride. The reaction mixture is stirred for 3 hours, left to stand overnight, then adjusted to pH 8 with aqueous sodium hydrogen carbonate solution and diluted with diethyl ether. The organic phase is washed neutral with water, dried over sodium sulphate and concentrated. Purification of the residue by chromatography on silica gel with hexane/ethyl acetate (vol. 4:1) yields 8.8 g of 2-[4-(isopropoxy)biphenyl]-5-[(tetrahydro-2-pyranyloxy)methyl]pyridine.

c) A solution of 8.2 g of 2-[4-(isopropoxy)biphenyl]-5-[(tetrahydro-2-pyranyloxy)methyl]pyridine in 150 ml of tetra- hydrofuran is treated with 22 ml of 2N hydrochloric acid. The mixture is stirred at 60° C. for 6 hours, then diluted with diethyl ether, washed twice with 50 ml of saturated aqueous sodium hydrogen carbonate solution each time and three times with 75ml of water each time, dried over sodium sulphate and concentrated. 7.2 g of 6-[4-(isopropoxy)biphenyl]-3-pyridinecarbinol are obtained.

d) A solution of 7.2 g of 6-[4-(isopropoxy)biphenyl]-3-pyridinecarbinol in 150 ml of 1,2-dichloroethane is treated with 9.6 g of activated manganese(IV) oxide. The suspension is heated to boiling for 4.5 hours and then filtered. Concentration of the filtrate gives 6.0 g of 6-[4-(isopropoxy)biphenyl]-3-pyridinecarboxaldehyde.

e) 6.0 g of 6-[4-(isopropoxy)biphenyl]-3-pyridinecarbox- aldehyde, 7.9 g of butyltriphenylphosphonium chloride, 2.5 g of potassium tert.-butylate and 100 ml of tert.-butyl methyl ether are reacted in an analogous manner to Example 1(b) to give 5.7 g of 2-[4-(isopropoxy)-4'-biphenyl]-5-(pentenyl)pyridine as a cis/trans mixture.

f) 5.7 g of 2-[4-(isopropoxy)-4'-biphenyl]-5-(pentenyl)-pyridine, 1 g of palladium on active charcoal (10 w/w %) and 100 ml of ethyl acetate are hydrogenated in an analogous manner to Example 4(c) to give 5.3 g of 2-[4-(isopropoxy)-4'-biphenyl]-5-(pentenyl)pyridine.

g) 5.3 g of 2-[4-(isopropoxy)-4'-biphenyl]-5-(pentenyl)pyridine, 7.0 g of boron tribromide in 100 ml of dichloromethane are reacted in an analogous manner to Example 1(f) to give 3.7 g of 4-(5-pentyl-2-pyridinyl)-4'-hydroxybiphenyl.

The following compounds can be manufactured in an analogous manner:

4-[5-Pentyl-2-pyridinyl]-4'-biphenyl acetate;
4-[5-pentyl-2-pyridinyl]-4'-biphenyl propionate;
4-[5-pentyl-2-pyridinyl]-4'-biphenyl butanoate;
4-[5-pentyl-2-pyridinyl]-4'-biphenyl pentanoate;
4-[5-pentyl-2-pyridinyl]-4'-biphenyl heptanoate;
4-[5-pentyl-2-pyridinyl]-4'-biphenyl octanoate;
4-[5-pentyl-2-pyridinyl]-4'-biphenyl decanoate;
4-[5-pentyl-2-pyridinyl]-4'-biphenyl undecanoate;
4-[5-pentyl-2-pyridinyl]-4'-biphenyl dodecanoate;
4-(5-heptyl-2-pyridinyl)-4-biphenyl acetate;
4-(5-heptyl-2-pyridinyl)-4-biphenyl propanoate;
4-(5-heptyl-2-pyridinyl)-4-biphenyl butanoate;
4-(5-heptyl-2-pyridinyl)-4-biphenyl pentanoate;
4-(5-heptyl-2-pyridinyl)-4-biphenyl hexanoate;
4-(5-heptyl-2-pyridinyl)-4-biphenyl heptanoate;
4-(5-heptyl-2-pyridinyl)-4-biphenyl octanoate;
4-(5-heptyl-2-pyridinyl)-4-biphenyl nonanoate;
4-(5-heptyl-2-pyridinyl)-4-biphenyl decanoate;
4-(5-heptyl-2-pyridinyl)-4-biphenyl undecanoate;
4-(5-heptyl-2-pyridinyl)-4-biphenyl dodecanoate;
1-(5-hexyl-2-pyridinyl)-4-phenyl (2E)-heptenoate;
1-(5-hexyl-2-pyridinyl)-4-phenyl (2E)-octenoate;
1-(5-hexyl-2-pyridinyl)-4-phenyl (2E)-nonenoate;
1-(5-heptyl-2-pyridinyl)-4-phenyl (2E)-butenoate, m.p. (C-N) 72° C., cl.p. (N-I) 93° C.;
1-(5-heptyl-2-pyridinyl)-4-phenyl (2E)-pentenoate, m.p. (C-N) 70° C., cl.p. (N-I) 75° C.;
1-(5-heptyl-2-pyridinyl)-4-phenyl (2E)-hexenoate, m.p. (C-N) 67° C., cl.p. (N-I) 87° C.;
1-(5-heptyl-2-pyridinyl)-4-phenyl (2E)-heptenoate, m.p. (C-N) 67° C., cl.p. (N-I) 79° C.;
1-(5-heptyl-2-pyridinyl)-4-phenyl (2E)-octenoate, m.p. (C-N) 58° C., $S_2$-S (44° C.), cl.p. (N-I) 87° C.;
1-(5-heptyl-2-pyridinyl)-4-phenyl (2E)-nonenoate;
1-(5-heptyl-2-pyridinyl)-4-phenyl (2E)-decenoate, $S_2$-N 59° C., cl.p. (N-I) 87° C.;
1-(5-heptyl-2-pyridinyl)-4-phenyl (2E)-dodecenoate, $S_2$-$S_C$ 57° C., $S_C$-N 66° C., cl.p. (N-I) 87° C.;
1-(5-octyl-2-pyridinyl)-4-phenyl (2E)-butenoate, m.p. (C-N) 54° C., cl.p. (N-I) 89° C.;
1-(5-octyl-2-pyridinyl)-4-phenyl (2E)-pentenoate, m.p. (C-$S_2$) 57° C., $S_2$-N (33° C.), cl.p. (N-I) 72° C.;
1-(5-octyl-2-pyridinyl)-4-phenyl (2E)-hexenoate;
1-(5-octyl-2-pyridinyl)-4-phenyl (2E)-heptenoate;
1-(5-octyl-2-pyridinyl)-4-phenyl (2E)-octenoate, m.p. (C-N) 62° C., $S_C$-N (46° C.), cl.p. (N-I) 83° C.;
1-(5-octyl-2-pyridinyl)-4-phenyl (2E)-nonenoate;
1-(5-octyl-2-pyridinyl)-4-phenyl (2E)-decenoate;

1-(5-octyl-2-pyridinyl)-4-phenyl (2E)-undecenoate;
1-(5-octyl-2-pyridinyl)-4-phenyl (2E)-dodecenoate;
1-(5-nonyl-2-pyridinyl)-4-phenyl (2E)-butenoate;
1-(5-nonyl-2-pyridinyl)-4-phenyl (2E)-pentenoate;
1-(5-nonyl-2-pyridinyl)-4-phenyl (2E)-hexenoate;
1-(5-nonyl-2-pyridinyl)-4-phenyl (2E)-heptenoate;
1-(5-nonyl-2-pyridinyl)-4-phenyl (2E)-octenoate, m.p. (C-N) 62° C., $S_2$-$S_C$(47° C.), $S_C$-N (57° C.), cl.p. (N-I) 86° C.;
1-(5-nonyl-2-pyridinyl)-4-phenyl (2E)-nonenoate;
1-(5-nonyl-2-pyridinyl)-4-phenyl (2E)-decenoate;
1-(5-nonyl-2-pyridinyl)-4-phenyl (2E)-undecenoate;
1-(5-nonyl-2-pyridinyl)-4-phenyl (2E)-dodecenoate.

EXAMPLE 5

In order to investigate the properties of the compounds of formula I, a basic mixture is prepared and mixed with in each case 20% of a compound of formula I. The phase transition temperatures of these mixtures are determined, the crystal- lization temperature $T_c$ is determined from conductivity data. The switching times are measured at 25° C. (10 vpp/μ, time from the start of the pulse to maximum current). The measured values are compiled in Table 1.

| Basic Mixture |
| --- |
| 27.6 wt. % of bis[(S)-1-methylheptyl]-p-terphenyl 4,4'-dicarboxylic acid ester |
| 18.4 wt. % of 2-[4-(hexyloxy)phenyl]-5-nonylpyrimidine |
| 18.4 wt. % of 2-[4-(nonyloxy)phenyl]-5-nonylpyrimidine |
| 9.2 wt. % of 2-[4-(nonyloxy)phenyl]-5-octylpyrimidine |
| 9.2 wt. % of 2-[4-(heptyloxy)phenyl]-5-heptylpyrimidine |
| 9.2 wt. % of 2-[4-(decyloxy)phenyl]-5-octylpyrimidine |
| 8.0 wt. % of 4-(decyloxy)benzoic acid 4-(2-[trans-4-pentylcyclohexyl]-1-ethyl)phenyl ester. |

TABLE 1

A $H_{11}C_5COO$—⟨phenyl⟩—CH=N—⟨phenyl⟩—$C_5H_{11}$

| | C/$S_X$-$S_C$* (°C.) | $S_C$*-$S_A$ (°C.) | $S_A$-I (°C.) | $P_s$ nC/cm² | Switching time μsec |
| --- | --- | --- | --- | --- | --- |
| Basic mixture | −11 | 59 | 65 | 90 | 62 |
| Basic mixture + 20 wt. % (A) | −12 | 66 | 71 | 77 | 40 |

I claim:

1. A compound of the formula

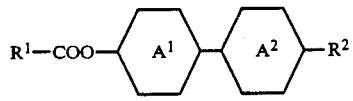

wherein
$R^1$ is alkenyl with 2 to 12 carbon atoms;
$R^2$ is alkyl with 1 to 12 carbon atoms or alkenyl with 2 to 12 carbons atoms, in which at least one methylene group can be replaced by —O—;
$A^1A^2$ each independently is 1,4-phenylene which is unsubstituted or substituted with at least one halogen, or pyridine-2,5-diyl or pyrimidine-2,5-diyl;
with the proviso that only one of the rings $A^1$ or $A^2$ is either pyridine-2,5-diyl or pyrimidine-2,5-diyl.

2. The compound according to claim 1, wherein $R^2$ is alkyl with 1 to 7 carbon atoms or alkenyl with 2 to 7 carbon atoms.

3. The compound according to claim 1, wherein $R^1$ is 1E-alkenyl.

4. The compound according to claim 1 of the formula

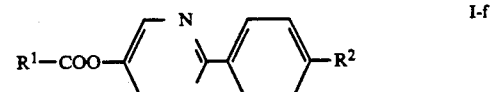

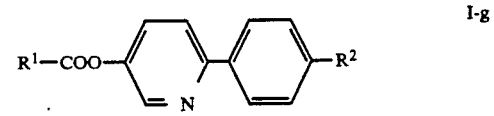

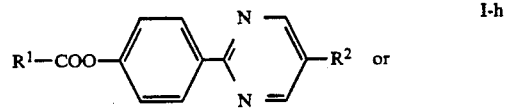

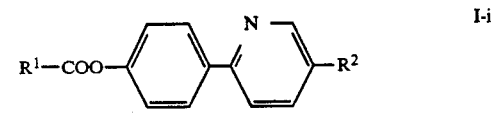

5. The compound according to claim 1, wherein the compound is (E)-Oct-2-enoic acid 4-(5-nonyl-pyrimidyn-2-yl)-phenyl ester.

6. The liquid crystalline mixture containing at least two components, wherein at least one component has the formula

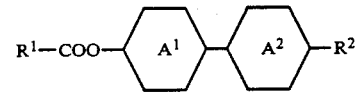

wherein
$R^1$ is alkenyl with 2 to 12 carbon atoms;
$R^2$ is alkyl with 1 to 12 carbon atoms or alkenyl with 2 to 12 carbons atoms, in which at least one methylene group can be replaced by —O—;
$A^1$, $A^2$ each independently is 1,4-phenylene which is unsubstituted or substituted with at least one halogen, or pyridine-2,5-diyl or pyrimidine-2,5-diyl;
with the proviso that only one of the rings $A^1$ or $A^2$ is either pyridine-2,5-diyl or pyrimidine-2,5-diyl .

7. The liquid crystalline mixture according to claim 6, wherein the at least one component is (E) -Oct-2-enoic acid 4- (5-nonyl-pyrimidyn-2-yl)-phenyl ester.

* * * * *